(12) United States Patent
Mitra et al.

(10) Patent No.: US 6,426,326 B1
(45) Date of Patent: Jul. 30, 2002

(54) LIQUID CLEANSING COMPOSITION COMPRISING LAMELLAR PHASE INDUCING STRUCTURANT WITH LOW SALT CONTENT AND ENHANCED LOW TEMPERATURE STABILITY

(75) Inventors: Shuman Mitra, San Jose, CA (US); Sudhakar Puvvada, Shelton, CT (US)

(73) Assignee: Unilever Home & Person Care USA, a division of Conopco, Inc., Greenwich, CT (US)

( * ) Notice: Subject to any disclaimer, the term of this patent is extended or adjusted under 35 U.S.C. 154(b) by 177 days.

(21) Appl. No.: 09/632,061

(22) Filed: Aug. 3, 2000

Related U.S. Application Data

(60) Provisional application No. 60/154,265, filed on Sep. 16, 1999, now abandoned.

(51) Int. Cl.[7] ............................ C11D 7/50; C11D 17/00; C11D 15/00; C11D 10/00; A61K 7/50
(52) U.S. Cl. ...................... 510/130; 510/158; 510/159; 510/417; 510/426; 510/488; 510/491; 510/537
(58) Field of Search ............................... 510/130, 158, 510/159, 417, 426, 488, 491, 537

(56) References Cited

U.S. PATENT DOCUMENTS

| | | | |
|---|---|---|---|
| 4,243,549 A | | 1/1981 | Messenger et al. |
| 4,375,421 A | | 3/1983 | Rubin et al. |
| 5,147,576 A | * | 9/1992 | Montague et al. ........... 252/174 |
| 6,150,312 A | * | 11/2000 | Puvvada et al. ............ 510/130 |
| 6,174,846 B1 | * | 1/2001 | Villa .......................... 510/159 |

FOREIGN PATENT DOCUMENTS

| | | |
|---|---|---|
| WO | 96/31187 | 10/1996 |
| WO | 97/05857 | 2/1997 |
| WO | 98/13022 | 4/1998 |

OTHER PUBLICATIONS

International Search Report PCT/EP 00/08266 (Aug. 23, 2000).
Co–pending application: Puvvada et al.; Ser. No.: 09/286, 042; Filed: Apr. 5, 1999: Liquid Composition with Enhanced Low Temperature Stability.

* cited by examiner

*Primary Examiner*—Mark Kopec
*Assistant Examiner*—John M Petruncio
(74) *Attorney, Agent, or Firm*—Alan A. Bornstein

(57) ABSTRACT

The invention relates to liquid cleansing compositions in lattellar phase which possess a lotion-like appearance conveying signals of enhanced moisturization. However, these liquids often undergo an irreversible decrease in viscosity under freeze/thaw conditions, losing their moisturization signals. The use of low salt levels in amphoteric and anionic surfactants in a structured liquid product has been found to improve its freeze/thaw stability.

27 Claims, No Drawings

LIQUID CLEANSING COMPOSITION COMPRISING LAMELLAR PHASE INDUCING STRUCTURANT WITH LOW SALT CONTENT AND ENHANCED LOW TEMPERATURE STABILITY

This application claims the benefit of U.S. Provisional Application No. 60/154,265, filed Sep. 16, 1999 abandoned.

BACKGROUND

1. Field of the Invention

The present invention relates to liquid cleansing compositions of the type typically used in skin cleansing or shower gel compositions which compositions are "structured" lamellar phase compositions.

2. Background of the Invention

The rheological behavior of all surfactant solutions, including liquid cleansing solutions, is strongly dependent on the microstructure, i.e., the shape and concentration of micelles or other self-assembled structures in solution.

When there is sufficient surfactant to form micelles (concentrations above the critical micelle concentration or CMC), for example, spherical, cylindrical (rod-like) or discoidal micelles may form. As surfactant concentration increases, ordered liquid crystalline phases such as lamellar phase, hexagonal phase or cubic phase may form. The lamellar phase, for example, consists of alternating surfactant bilayers and water layers. These layers are not generally flat but fold to form submicron spherical onion like structures called vesicles or liposomes. The hexagonal phase, on the other hand, consists of long cylindrical micelles arranged in a hexagonal lattice. In general, the microstructure of most personal care products consist of either spherical micelles; rod micelles; or a lamellar dispersion.

As noted above, micelles may be spherical or rod-like. Formulations having spherical micelles tend to have a low viscosity and exhibit Newtonian shear behavior (i.e., viscosity stays constant as a function of shear rate; thus, if easy pouring of product is desired, the solution is less viscous and, as a consequence, it doesn't suspend as well). In these systems, the viscosity increases linearly with surfactant concentration.

Rod micellar solutions are more viscous because movement of the longer micelles is restricted. At a critical shear rate, the micelles align and the solution becomes shear thinning. Addition of salts increases the size of the rod micelles thereof increasing zero shear viscosity (i.e., viscosity when sitting in bottle) which helps suspend particles but also increases critical shear rate (point at which product becomes shear thinning; higher critical shear rates means product is more difficult to pour).

Lamellar dispersions differ from both spherical and rod-like micelles because they can have high zero shear viscosity (because of the close packed arrangement of constituent lamellar droplets), yet these solutions are very shear thinning (readily dispense on pouring). That is, the solutions can become thinner than rod micellar solutions at moderate shear rates.

In formulating liquid cleansing compositions, therefore, there is the choice of using rod-micellar solutions (whose zero shear viscosity, e.g., suspending ability, is not very good and/or are not very shear thinning); or lamellar dispersions (with higher zero shear viscosity, e.g. better suspending, and yet are very shear thinning). Such lamellar compositions are characterized by high zero shear viscosity (good for suspending and/or structuring) while simultaneously being very shear thinning such that they readily dispense in pouring. Such compositions possess a "heaping", lotion-like appearance which convey signals of enhanced moisturization.

To form such lamellar compositions, however, some compromises have to be made. First, generally higher amounts of surfactant are required to form the lamellar phase. Thus, it is often needed to add auxiliary surfactants and/or salts which are neither desirable nor needed. Second, only certain surfactants will form this phase and, therefore, the choice of surfactants is restricted.

In short, lamellar compositions are generally more desirable (especially for suspending emollient and for providing consumer aesthetics), but more expensive in that they generally require more surfactant and are more restricted in the range of surfactants that can be used.

When rod-micellar solutions are used, they also often require the use of external structurants to enhance viscosity and to suspend particles (again, because they have lower zero shear viscosity than lamellar phase solutions). For this, carbomers and clays are often used. At higher shear rates (as in product dispensing, application of product to body, or rubbing with hands), since the rod-micellar solutions are less shear thinning, the viscosity of the solution stays high and the product can be stringy and thick. Lamellar dispersion based products, having higher zero shear viscosity, can more readily suspend emollients and are typically more creamy. Again, however, they are generally more expensive to make (e.g., they are restricted as to which surfactants can be used and often require greater concentration of surfactants).

In general, lamellar phase compositions are easy to identify by their characteristic focal conic shape and oily streak texture while hexagonal phase exhibits angular fan-like texture. In contrast, micellar phases are optically isotropic.

It should be understood that lamellar phases may be formed in a wide variety of surfactant systems using a wide variety of lamellar phase "inducers" as described, for example, in U.S. Pat. No. 5,952,286 titled "Liquid Cleansing Composition Comprising Soluble, Lamellar Phase Inducing Structurant" by Sudhakar Puvvada, et al., issued Sep. 14, 1999. Generally, the transition from micelle to lamellar phase are functions of effective average area of headgroup of the surfactant, the length of the extended tail, and the volume of tail. Using branched surfactants or surfactants with smaller headgroups or bulky tails are also effective ways of inducing transitions from rod micellar to lamellar.

One way of characterizing lamellar dispersions include measuring viscosity at low shear rate (using for example a Stress Rheometer) when additional inducer (e.g., oleic acid or isostearic acid) is used. At higher amounts of inducer, the low shear viscosity will significantly increase.

Another way of measuring lamellar dispersions is using freeze fracture electron microscopy. Micrographs generally will show lamellar microstructure and close packed organization of the lamellar droplets (generally in size range of about 2 microns).

One problem with certain lamellar phase compositions is that they tend to lose their lamellar stability in colder temperatures (e.g., 0 to 45° F.). While not wishing to be bound by theory, this may be because, in cold conditions, the oil droplets become less flexible and the spherical structure characterizing the lamellar interaction breaks into lamellar sheets instead.

BRIEF DESCRIPTION OF THE INVENTION

Applicants have discovered that the use of surfactants containing low salt levels enhances freeze/thaw stability in personal wash structured liquid formulations. The ability of a structured liquid to maintain viscosity under freeze/thaw conditions is extremely desirable to demonstrate moisturization and aesthetics. Applicants have found that the combination of amphoteric and anionic surfactants, and either soluble or insoluble lamellar structurants, with oil creates a stable structured liquid with excellent freeze/thaw viscosity stability in conjunction with low overall salt content.

For example, when low salt cocamidopropyl betaine is added to a liquid formulation containing the following compounds: an anionic surfactant like sodium lauryl ether sulfate, high levels of an emollient such as sunflower seed oil, and a lamellar structurant fatty acid like lauric or isostearic acid; a structured liquid with excellent freeze/thaw viscosity is produced. The role of salt (e.g. NaCl) in the cocamidopropyl betaine to affect this stability is clearly seen by the poor freeze/thaw stability of the structured liquids containing higher salt containing cocamidopropyl betaine. Likewise, when low salt sodium lauryl ether sulfate is added to a similar liquid formulation with sodium lauroamphoacetate, the formulation exhibits improved freeze thaw stability. Furthermore, the presence of salt separately added to the lamellar formula also worsens the freeze thaw stability. Therefore, the structured liquids containing surfactants with low salt levels, preferably under about 1.1 weight %, are stable after being subjected to low temperatures, especially with regard to their viscosity.

It has further been found that this generally inverse relationship with salt and freeze thaw viscosity stability is not applicable where branched anionic surfactants comprise about 50% to 100% of the anionic surfactant in the structured formulation. These anionic surfactants include branched $C_{10}-C_{22}$, preferably branched $C_{10}-C_{16}$ alkyl, alkali metal ether sulfates (i.e., having at least one branch from the alkyl portion of the alkyl ether sulfate). Such anionic surfactants already provide enhanced freeze thaw stability in structured liquid compositions relative to compositions not comprising the branched $C_{10}-C_{22}$ alkyl, alkali metal ether sulfate as disclosed by the Applicant in copending U.S. patent application Ser. No. 09/286042.

More specifically, the invention comprises a liquid cleansing composition, wherein the liquid is in a lamellar phase, comprising a surfactant system, preferably a system which contains at least about 5 weight percent of surface active compounds. The inventive composition also includes an amphoteric and/or zwitterionic surfactant present at about 3 to 30 weight percent. The inventive composition also contains at least one or more anionic surfactants present at about 2 to 40 weight percent. The inventive composition also contains a lamellar structurant compound present at about 0.5 to 10 weight percent. The inventive composition has a initial viscosity in the range of about 15,000 to 300,000 centipoises (cps) measured at 0.5 RPM using T-bar spindle A using the procedure described below. The inventive composition also has a freeze thaw viscosity (measured after at least one cycle of 0° F. to 70 F.) having a percent drop (if any) relative to initial viscosity of no more than about 35 percent. Initial viscosity is here defined as that obtained at 70 F. for the inventive composition which has never been frozen. Freeze thaw viscosity is likewise defined as the viscosity obtained after at least one freeze thaw cycle.

The inventive composition also has a strong electrolyte concentration of about 1.1 weight percent or less. Alternatively the inventive composition has a weight percent ratio of anionic surfactant to strong electrolyte in the range of 8:1 to 100:1, preferably 10:1 to 50:1. Similarly, the inventive composition has a weight percent ratio of amphoteric surfactant to strong electrolyte in the range of 3:1 to 100:1, preferably 5:1 to 50:1. Strong electrolytes are those salts which are completely dissociated in a liquid cleansing composition. Such salts include ammonium, alkali and alkaline earth chlorides and sulfates. As the term is used here, strong electrolyte is defined as the total amount of chloride and sulfate in the inventive composition derived from any source, expressed as a weight percent. Preferably, the strong electrolyte content is minimized by the use of either a low salt amphoteric, zwitterionic, or anionic surfactant, or a blend thereof; in the inventive composition. A low salt surfactant in the inventive formula is alternatively here defined by R being less than or equal to 0.15, where R=[% salt in surfactant]/[% active in surfactant]. For example, if a surfactant is 50% active which contains 1% salt, then the value of R for that surfactant is 0.02, and the surfactant is classified as a low salt surfactant. Percent active in a surfactant raw material is defined as the concentration of the desired ingredients in the raw material, as is well known in the art.

DETAILED DESCRIPTION OF THE INVENTION

The present invention relates to liquid lamellar cleansing compositions, wherein the liquid is in a lamellar phase, comprising a surfactant system, preferably a system which contains at least about 5 weight percent, preferably at least about 10 weight percent of surface active compounds. The inventive composition also includes an amphoteric and/or zwitterionic surfactant. Preferably the amphoteric or zwitterionic surfactant, or a blend thereof is present at about 3 to 30 weight percent, more preferably at about 5 to 20 weight percent. The inventive composition also contains at least one anionic surfactant. Preferably the anionic surfactant is present at about 2 to 40 weight percent, more preferably at about 5 to 20 weight percent. The inventive composition also contains a lamellar structurant. Preferably the lamellar structurant is present at about 0.5 to 10 weight percent, more preferably at about 0.5 to 5 weight percent.

The inventive composition has a initial viscosity in the range of about 15,000 to 300,000 centipoises (cps) measured at 0.5 RPM using T-bar spindle A using the procedure described below. The initial viscosity is preferably 30,000 to 150,000 cps, more preferably from about 60,000 to about 140,000 cps. The inventive composition also has a freeze thaw viscosity (measured after at least one cycle, preferably after at least 2 cycles, more preferably after 3 cycles of 0° F. to 70 F. freeze thaw cycles) having a percent drop (if any) relative to initial viscosity of no more than about 35 percent.

The inventive composition also has a strong electrolyte concentration of about 1.1 weight percent or less. Alternatively the inventive composition has a weight percent ratio of anionic surfactant to strong electrolyte in the range of 8:1 to 100:1, preferably 10:1 to 50:1. Similarly, the inventive composition has a weight percent ratio of amphoteric surfactant to strong electrolyte is in the range of 3:1 to 100:1, preferably 5:1 to 50:1. Preferably, the strong electrolyte content is controlled by the use of either a low salt amphoteric, zwitterionic, or anionic surfactant, or a blend thereof; in the inventive composition.

Surfactants

The surfactant system of the subject invention comprises 5 to 70% by weight, preferably 10 to 30% by wt. of the composition and comprises:
 (a) at least one anionic surfactant;
 (b) At least one amphoteric and/or zwitterionic surfactant;
 (c) At least one lamellar structurant compound; and
 (d) optionally one or more nonionic surfactants, cationic surfactants, or blends thereof.

The anionic surfactant (which may comprise 2 to 40% by wt. of total composition) may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or an aromatic sulfonate such as alkyl benzene sulfonate, and the like.

The anionic may also be an alkyl sulfate (e.g., $C_{12}$–$C_{18}$ alkyl sulfate) or alkyl ether sulfate (including alkyl glyceryl ether sulfates), and the like. Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates, and the like.

Sulfosuccinates may be monoalkyl sulfosuccinates having the formula:

$$R^4O_2CCH_2CH(SO_3M)CO_2M;$$

amido-MEA sulfosuccinates of the formula $$R^4CONHCH_2CH_2O_2CCH_2CH(SO_3M)CO_2M$$

wherein $R^4$ ranges from $C_8$–$C_{22}$ alkyl and M is a solubilizing cation;

amido-MIPA sulfosuccinates of formula $$RCONH(CH_2)CH(CH_3)(SO_3M)CO_2M$$

where M is as defined above.

Also included are the alkoxylated citrate sulfosuccinates; and alkoxylated sulfosuccinates such as the following:

$$R\text{—}O\text{—}(CH_2CH_2O)_n\overset{\overset{O}{\|}}{C}CH_2CH(SO_3M)CO_2M$$

wherein n=1 to 20; and M is as defined above.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula $$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

$$R\text{—}(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ$^{(R)}$ by Seppic.

Another surfactant which may be used are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in U.S. Pat. No. 5,393,466, Titled "Fatty Acid Esters Of Polyalkoxylated Isethionic Acid" issued Feb. 28, 1995 to Ilardi et al., hereby incorporated by reference into the subject application. This compound has the general formula:

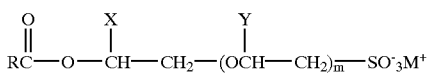
$$\overset{O}{\underset{\|}{R}C}\text{—}O\text{—}\overset{X}{\underset{|}{C}H}\text{—}CH_2\text{—}(O\overset{Y}{\underset{|}{C}H}\text{—}CH_2)_{\overline{m}}\text{—}SO^-_3M^+$$

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

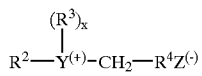
$$R^2\text{—}\overset{\overset{(R^3)_x}{|}}{Y^{(+)}}\text{-}CH_2\text{—}R^4Z^{(-)}$$

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl) ammonio]-butane-1-carboxylate;
3-[S-ethyl-S-(3-dodecoxy-2-hydroxyprbpyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

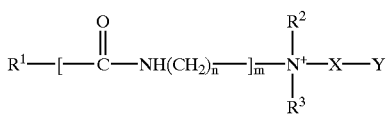

where R' is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is —$CO_2$— or —$SO_3$—

Suitable amphoteric detergents within the above general formula include simple betaines of formula:

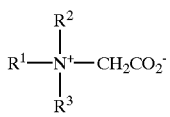

and amido betaines of formula:

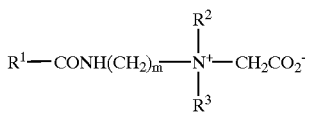

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl. A suitable betaine is cocoamidopropyl betaine.

A further possibility is that the amphoteric detergent is a sulphobetaine of formula

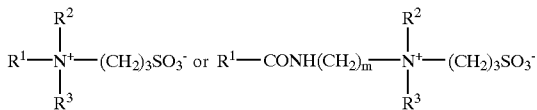

where m is 2 or 3, or variants of these in which —$(CH_2)_3SO^-_3$ is replaced by

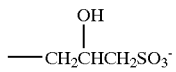

In these formulae $R^1$, $R^2$ and $R^3$ are as discussed previously.

Amphoacetates and diamphoacetates are also intended to be covered in possible zwitterionic and/or amphoteric compounds which may be used, especially C8–C20 amphoacetates or mixtures thereof, and the like. A suitable amphoacetate is sodium laurylamphoacetate.

The amphoteric/zwitterionic surfactant, when used, generally comprises 3 to 30%, preferably 5 to 20% by weight, more preferably 10 to 20% of the composition.

A preferred surfactant system of the invention comprises the following: anionic surfactant (e.g. alkali metal alkyl ethersulfate)—2–50% amphoteric surfactant (e.g. alkyl betaine or alkyl amphoacetate)—3–20%.

The surfactant system may also optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides, and the like.

The nonionic may also be a sugar amide, such as a polysaccharide amide. Specifically, the surfactant may be one of the lactobionamides described in U.S. Pat. No. 5,389,279 titled "Compositions comprising nonionic glycolipid surfactants" issued on Feb. 14, 1995 to Au et al. which is hereby incorporated by reference or it may be one of the sugar amides described in U.S. Pat. No. 5,009,814 titled "Use of n-polyhydroxyalkyl fatty acid amides as thickening agents for liquid aqueous surfactant systems" issued on Apr. 23, 1991 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 titled "Foaming surfactant compositions", issued on Jan. 21, 1986 to Llenado, both of which are also incorporated into the subject application by reference.

Preferred alkyl polysaccharides are alkylpolyglycosides of the formula

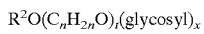

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

The nonionic preferably comprises 0 to 10% by wt. of the composition.

Lamellar Structurant

The compositions of the invention utilize about 0.5% to 10% by wt., preferably 0.5 to 5% by wt. of a structuring agent which works in the compositions to form a lamellar phase. Such lamellar phase enables the compositions to suspend particles more readily (e.g., emollient particles) while still maintaining good shear thinning properties. The lamellar phase also provides consumers with desired rheology ("heaping").

The structurant is preferably a fatty acid or ester derivative thereof, a fatty alcohol, or trihydroxystearin, and the like. More preferably the structurant is selected from the group consisting of lauric or isostearic acid, or trihydroxystearin.

Examples of fatty acids which may be used are $C_{10}$–$C_{22}$ acids such as the following: lauric acid, oleic acid, isostearic acid, linoleic acid, linolenic acid, ricinoleic acid, elaidic acid, arichidonic acid, myristoleic acid and palmitoleic acid, and the like. Ester derivatives include propylene glycol isostearate, propylene glycol oleate, glyceryl isostearate, glyceryl oleate and polyglyceryl diisostearate, and the like.

Oil/Emollient

One of the principle benefits of the invention is the ability to suspend oil/emollient particles in a lamellar phase composition. The following oil/emollients may optionally be suspended in the compositions of the invention.

Various classes of oils are set forth below.

Vegetable oils: Arachis oil, castor oil, cocoa butter, coconut oil, corn oil, cotton seed oil, olive oil, palm kernel oil, rapeseed oil, safflower seed oil, sesame seed oil and soybean oil, and the like.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate, and the like.

Animal Fats: acetylated lanolin alcohols, lanolin, lard, mink oil and tallow, and the like.

Other examples of oil/emollients include mineral oil, petrolatum, silicone oil such as dimethyl polysiloxane, lauryl and myristyl lactate, and the like.

The emollient/oil is generally used in an amount from about 0 to 70%, preferably 5 to 40% by wt. of the composition. Generally, it should comprise no more than 70% of the composition.

In addition, the compositions of the invention may include optional ingredients as follows:

Organic solvents, such as ethanol; auxiliary thickeners, sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters.

Antioxidants such as, for example, butylated hydroxytoluene (BHT) may be used advantageously in amounts of about 0.01% or higher if appropriate.

Cationic conditioners which may be used include Quatrisoft LM-200 Polyquaternium-24, Merquat Plus 3330—Polyquaternium 39; and Jaguar$^{(R)}$ type conditioners.

Another optional ingredient which may be added are the deflocculating polymers such as are taught in U.S. Pat. No. 5,147,576 titled "Liquid Detergent Composition In The Form Of Lamellar Droplets Containing A Deflocculating Polymer", issued on Sep. 15, 1992 to Montague, hereby incorporated by reference.

Other ingredients which may be included are exfoliants such as polyoxyethylene beads, walnut sheets and apricot seeds, and the like.

The compositions of the invention, as noted, are lamellar compositions. In particular, the lamellar phase comprises 20 to 80%, preferably 30 to 65% of the total phase volume. The phase volume may be measured, for example, by conductivity measurements or other measurements which are well known to those skilled in the art. While not wishing to be bound by theory, higher phase volume is believed to provide better suspension of emollients.

The invention will now be described in greater detail by way of the following non-limiting examples. The examples are for illustrative purposes only and not intended to limit the invention in any way.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

All percentages in the specification and examples are intended to be by weight unless stated otherwise.

EXAMPLES

EXAMPLES 1–2

The following table clearly shows the effect of low salt cocamidopropyl betaine (containing approx 0.8% NaCl) in enhancing freeze thaw viscosity stability of a lamellar structured liquid formulation using lauric acid as the lamellar structurant, compared to the same formulation using a conventional, commercially available cocamidopropyl betaine with a residual salt level of 5–6%. Comparing Examples 1 and 2, we find a 50% drop in viscosity in the formulations with high salt versus an 8.3% drop in viscosity in the formulations with low salt under freeze thaw conditions.

R=% salt in surfactant/% active in surfactant.

|  | Weight Percent | |
| --- | --- | --- |
| Example # | 1 | 2 |
| Component | Inventive | Comparative |
| Sodium lauryl ether sulfate @70% | 9 | 9 |
| Cocamidopropyl betaine @30% | 0 | 13.5<br>R = 0.177 |
| Low salt Cocamidopropyl betaine @31% | 13.5<br>R = 0.025 | 0 |
| Sunflower oil | 15 | 15 |
| Lauric acid | 3.2 | 3.2 |

-continued

| Example # | Weight Percent | |
|---|---|---|
| | 1 | 2 |
| Citric acid | 1.7 | 1.7 |
| RT viscosity (T-bar), cps | 76800 | 44800 |
| Freeze thaw viscosity (T-bar), cps | 70400 | 22400 |
| % Total salt | 0.45 | 2.49 |
| % drop | 8.3 | 50 |

EXAMPLES 3–4

The following table clearly shows the effect of low salt cocamidopropyl betaine in enhancing freeze thaw viscosity stability of a lamellar structured liquid formulation using isostearic acid as the lamellar structurant, compared to the same formulation with a conventional, commercially available cocamidopropyl betaine with a residual salt level of 5–6%: In this example, an increase in freeze thaw viscosity is obtained with the low salt betaine, whereas the regular betaine provides a freeze thaw product which is unstable with respect to viscosity, etc.

| Example # | Weight Percent | |
|---|---|---|
| | 3 | 4 |
| Component | Inventive | Comparative |
| Sodium lauryl ether sulfate@70% | 9 | 9 |
| Cocamidopropyl betaine@30% | 0 | 13.5 R = 0.177 |
| Low salt Cocamidopropyl betaine@31% | 13.5 R = 0.025 | 0 |
| Sunflower oil | 15 | 15 |
| Lauric acid | 3 | 3 |
| Citric acid | 1.7 | 1.7 |
| RT viscosity (T-bar), cps | 51200 | 16000 |
| Freeze thaw viscosity (T-bar), cps | 60800 | 9600 unstable |
| % Total salt | 0.45 | 2.49 |
| % drop | 18.8 increase | 40 |

EXAMPLES 5–6

The following table depicts formulations where the level of oil was decreased 5%, with the structurant being lauric acid. Again, the formula with the regular betaine is freeze thaw unstable, whereas the one using the low salt betaine undergoes a freeze thaw viscosity loss of 22.2%:

| Example # | Weight Percent | |
|---|---|---|
| | 5 | 6 |
| Component | Inventive | Comparative |
| Sodium lauryl ether sulfate@70% | 9 | 9 |
| Cocamidopropyl betaine@30% | 0 | 13.5 R = 0.177 |
| Low salt Cocamidopropyl betaine@31% | 13.5 R = 0.025 | 0 |
| Sunflower oil | 5 | 5 |
| Lauric acid | 3.6 | 3.6 |
| Citric acid | 1.7 | 1.7 |
| RT viscosity (T-bar), cps | 28800 | 19200 |
| Freeze thaw viscosity (T-bar), cps | 22400 | 12800 unstable |
| % Total salt | 0.45 | 2.49 |
| % drop | 22.2 | 33.3 |

EXAMPLES 7–8

The following table depicts formulations with betaine with different amounts of salt. In the first example (#7) using low salt betaine there is a 5% increase in the freeze thaw viscosity whereas, in example #8 which used regular betaine, there is a 43% decrease in the freeze thaw viscosity which is related to the salt in the betaine.

| Example | Weight Percent | |
|---|---|---|
| | 7 | 8 |
| Component | Inventive | Comparative |
| Cocamidopropyl betaine@30% | 0 R = 0.177 | 13.5 |
| Low salt Cocamidopropyl betaine @31% | 13.5 R = 0.025 | 0 |
| Sodium lauryl ether sulfate@70% | 9 | 9 |
| Sunflower oil | 15 | 15 |
| Lauric acid | 3.2 | 3 |
| Glycerine | 2 | 2 |
| Fragrance | 1 | 1 |
| Guar hydroxypropyl Trimonium chloride | 0.5 | 0.5 |
| DMDM Hydantoin | 0.2 | 0.2 |
| EHDP | 0.02 | 0.02 |
| water | to 100 | t 100 |
| RT viscosity (T-bar), cps | 131200 | 22400 |
| Freeze thaw viscosity (T-bar), cps | 137600 | 12800 |
| % Total salt | 0.45 | 2.49 |
| % drop | 4.9 increase | 42.9 |

Viscosity measurements were made in accordance with the following protocol:

Viscosity Measurement

Scope

This method covers the measurement of the viscosity of the finished product.

Apparatus

Brookfield RVT Viscometer with Helipath Accessory;

Chuck, weight and closer assembly for T-bar attachment;

T-bar Spindle A;

Plastic cups diameter greater than 2.5 inches.

Procedure

1. Verify that the viscometer and the helipath stand are level by referring to the bubble levels on the back of the instrument.
2. connect the chuck/closer/weight assembly to the Viscometer (Note the left-hand coupling threads).
3. Clean Spindle A with deionized water and pat dry with a Kimwipe sheet. Slide the spindle in the closer and tighten.
4. Set the rotational speed at 0.5 RPM. In case of a digital viscometer (DV) select the % mode and press autozero with the motor switch on.
5. Place the product in a plastic cup with inner diameter of greater than 2.5 inches. The height of the product in the cup should be at least 3 inches. The temperature of the product should be 25° C.

6. Lower the spindle into the product (~¼ inches). Set the adjustable stops of the helipath stand so that the spindle does not touch the bottom of the plastic cup or come out of the sample.
7. Start the viscometer and allow the dial to make one or two revolutions before turning on the Helipath stand. Note the dial reading as the helipath stand passes the middle of its downward traverse.
8. Multiply the dial reading by a factor of 4,000 and report the viscosity reading in cps.

We claim:

1. An aqueous lamellar structured liquid composition, comprising:
    a surfactant selected from the group consisting of amphoteric, zwitterionic, or a mixture thereof;
    an anionic surfactant;
    a lamellar structurant selected from the group consisting of fatty acids, fatty esters, trihydroxystearin, fatty alcohols; and
    a strong electrolyte present in a concentration below a predetermined amount, said amount being sufficient to maintain 65% or greater of said liquid composition's initial viscosity after freeze thawing.

2. The composition of claim 1 wherein the strong electrolyte is equal to or below about 1.1 weight percent.

3. The composition of claim 1 wherein the weight percent ratio of anionic surfactant to strong electrolyte is in the range of 8:1 to 100:1.

4. The composition of claim 1 wherein the weight percent ratio of anionic surfactant to strong electrolyte is in the range of 10:1 to 50:1.

5. The composition of claim 1 wherein the weight percent ratio of amphoteric surfactant to strong electrolyte is in the range of 3:1 to 100:1.

6. The composition of claim 1 wherein the weight percent ratio of amphoteric surfactant to strong electrolyte is in the range of 5:1 to 50:1.

7. The composition of claim 1 wherein the amphoteric or zwitterionic surfactant is selected from either cocamidopropyl betaine, or an alkali metal salt of alkyl amphoacetate.

8. The composition of claim 1 wherein the total concentration of the amphoteric or zwitterionic surfactant is in the range of about 3 to 30 weight percent of the total composition.

9. The composition of claim 1 wherein the anionic surfactant is selected from the group consisting of alkali metal or ammonium alkyl ether sulfate, alkali metal or ammonium alkyl sarcosinate, alkali metal or ammonium alkyl sulfosuccinate, and alkali metal or ammonium alkyl sulfate.

10. The composition of claim 1 wherein at least one surfactant is selected from the group consisting of an amphoteric, zwitterionic, or anionic surfactant; and said at least one surfactant has an R value less than or equal to 0.15 where $$R = \frac{[\% \text{ salt in surfactant}]}{[\% \text{ active in surfactant}]}.$$

11. The composition of claim 1 wherein at least one surfactant is selected from the group consisting of sodium lauroamphoacetate or cocamidopropyl betaine; and said at least one surfactant has an R value less than or equal to 0.15 where $$R = \frac{[\% \text{ salt in surfactant}]}{[\% \text{ active in surfactant}]}.$$

12. The composition of claim 1 wherein the concentration of anionic surfactant is in the range of about 2 to 40 weight percent.

13. The composition of claim 1 wherein the lamellar structurant is selected from the group consisting of lauric acid, isostearic acid, trihydroxystearin, palm kernel acid, capric acid, oleic acid, and caprylic acid.

14. The composition of claim 1 wherein the concentration of lamellar structurant is in the range of about 0.5 to 10 weight percent.

15. The composition of claim 1 wherein said composition has an initial viscosity in the range of 15,000 to 300,000 (cps).

16. The composition of claim 1 wherein said composition has an initial viscosity in the range of 30,000 to 150,000 (cps).

17. The composition of claim 1 wherein said composition has an initial viscosity in the range of 60,000 to 140,000 (cps).

18. The composition of claim 1 wherein its freeze thaw viscosity is not less than 65% of said composition's initial viscosity after one freeze thaw cycle.

19. The composition of claim 1 wherein its freeze thaw viscosity is not less than 65% of said composition's initial viscosity after two freeze thaw cycle.

20. The composition of claim 1 wherein its freeze thaw viscosity is not less than 65% of said composition's initial viscosity after three freeze thaw cycles.

21. The composition of claim 1 wherein its freeze thaw viscosity is not less than 80% of said composition's initial viscosity after one freeze thaw cycle.

22. An aqueous lamellar structured liquid composition, comprising:
    at least 5 weight percent of surface active material;
    about 3 to 30 weight percent of one or more amphoteric, or zwiterionic surfactants or a blend thereof;
    about 2 to 40 weight percent of an anionic surfactant;
    about 0.5 to 10 weight percent of a lamellar structurant selected from the group consisting of fatty acids, fatty esters, fatty alcohols, or trihydroxystearin; and
    less than about 1.1 weight percent of a strong electrolyte.

23. The composition of claim 22 wherein the amphoteric surfactant is sodium lauroamphoacetate.

24. The composition of claim 22 wherein the zwitterionic surfactant is cocamidopropyl betaine.

25. The composition of claim 22 wherein the anionic surfactant is selected from the group consisting of alkali metal or ammonium alkyl ether sulfate, alkali metal or ammonium alkyl sarcosinate, alkali metal or ammonium alkyl sulfate, and alkali metal or ammonium alkyl sulfosuccinate.

26. The composition of claim 22 wherein at least one surfactant selected from the group consisting of an amphoteric, zwitterionic, or anionic surfactant; and said at least one surfactant has an R value less than or equal to 0.15 where $$R = \frac{[\% \text{ salt in surfactant}]}{[\% \text{ active in surfactant}]}.$$

27. The composition of claim 22 wherein at least one surfactant selected from the group consisting of sodium lauroamphoacetate or cocamidopropyl betaine; and said at least one surfactant has an R value less than or equal to 0.15 where $$R = \frac{[\% \text{ salt in surfactant}]}{[\% \text{ active in surfactant}]}.$$

* * * * *

UNITED STATES PATENT AND TRADEMARK OFFICE
CERTIFICATE OF CORRECTION

PATENT NO.    : 6,426,326 B1
DATED         : July 30, 2002
INVENTOR(S)   : Shuman Mitra and Sudhakar Puvvada It is certified that error appears in the above-identified patent and that said Letters Patent is hereby corrected as shown below:

<u>Title page,</u>
Item [57], ABSTRACT,
Line 2, which reads: "lattellar phase which possess a lotion-like appearance con-"
should read -- lamellar phase which possess a lotion-like appearance con- --

<u>Column 9,</u>
Line 22, which reads: "One of the principle benefits of the invention is the ability"
should read -- One of the principal benefits of the invention is the ability --

<u>Column 14,</u>
Line 50, which reads: "surfactant selected from the group consisting of an" should read
-- surfactant is seleted from the group consisting of an --
Line 58, which reads: "surfactant selected from the group consisting of sodium" should
read -- surfactant is selected from the group consisting of sodium --

Signed and Sealed this

Seventeenth Day of December, 2002

JAMES E. ROGAN
*Director of the United States Patent and Trademark Office*